(12) United States Patent
Ferree

(10) Patent No.: US 6,648,919 B2
(45) Date of Patent: Nov. 18, 2003

(54) TRANSPLANTATION OF ENGINEERED MENISCUS TISSUE TO THE INTERVERTEBRAL DISC

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/170,599

(22) Filed: Jun. 13, 2002

(65) Prior Publication Data

US 2002/0151981 A1 Oct. 17, 2002

Related U.S. Application Data

(63) Continuation-in-part of application No. 09/688,716, filed on Oct. 16, 2000, now Pat. No. 6,454,804.
(60) Provisional application No. 60/159,488, filed on Oct. 14, 1999.

(51) Int. Cl.[7] ................................................. A61F 2/44
(52) U.S. Cl. ................. 623/17.11; 623/908; 623/17.16; 424/93.7
(58) Field of Search .......................... 623/17.11–17.16, 623/908, 919, 16.11; 424/93.7

(56) References Cited

U.S. PATENT DOCUMENTS

| | | | |
|---|---|---|---|
| 2,677,369 A | 5/1954 | Knowles | 128/92 |
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Niebauer | 3/1 |
| 3,648,294 A | 3/1972 | Shahrestani | 3/1 |
| 3,855,638 A | 12/1974 | Pilliar | 3/1 |
| 3,867,728 A | 2/1975 | Stubstad et al. | 3/1 |
| 3,875,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,759,766 A | 7/1988 | Buettner-Janz et al. | 623/17 |
| 4,772,287 A | 9/1988 | Ray et al. | 623/17 |
| 4,801,299 A | 1/1989 | Brendel et al. | 623/16.11 |
| 4,863,477 A | 9/1989 | Monson | 623/17 |
| 4,874,389 A | 10/1989 | Downey | 623/17 |
| 4,904,260 A | 2/1990 | Ray et al. | 623/17 |
| 4,911,718 A | 3/1990 | Lee et al. | 623/17 |
| 4,917,704 A | 4/1990 | Frey et al. | 623/17 |
| 4,932,969 A | 6/1990 | Frey et al. | 623/17 |
| 4,946,378 A | 8/1990 | Hirayama et al. | 623/17 |
| 5,002,576 A | 3/1991 | Fuhrmann et al. | 623/17 |
| 5,035,716 A | 7/1991 | Downey | 623/17 |
| 5,047,055 A | 9/1991 | Bao et al. | 623/17 |
| 5,071,437 A | 12/1991 | Steffee | 623/17 |
| 5,108,438 A | 4/1992 | Stone | 623/17 |
| 5,123,926 A | 6/1992 | Pisharodi | 623/17 |
| 5,171,280 A | 12/1992 | Baumgartner | 623/17 |
| 5,171,281 A | 12/1992 | Parsons et al. | 623/17 |
| 5,192,326 A | 3/1993 | Bao et al. | 623/17 |
| 5,246,458 A | 9/1993 | Graham | 623/17 |
| 5,258,031 A | 11/1993 | Salib et al. | 623/17 |
| 5,258,043 A | 11/1993 | Stone | 623/66 |
| 5,314,477 A | 5/1994 | Marnay | 623/17 |
| 5,320,644 A | 6/1994 | Baumgartner | 623/17 |
| 5,370,697 A | 12/1994 | Baumgartner | 623/17 |
| 5,375,823 A | 12/1994 | Navas | 267/195 |
| 5,401,269 A | 3/1995 | Buttner-Janz et al. | 623/17 |
| 5,425,773 A | 6/1995 | Boyd et al. | 623/17 |
| 5,458,642 A | 10/1995 | Beer et al. | 623/17 |
| 5,464,439 A | 11/1995 | Gendler | 623/16.11 |
| 5,514,180 A | 5/1996 | Heggeness et al. | 623/17.11 |
| 5,534,028 A | 7/1996 | Bao et al. | 623/17 |
| 5,534,030 A | 7/1996 | Navarro et al. | 623/17 |
| 5,545,229 A | 8/1996 | Parsons et al. | 623/17.11 |
| 5,556,431 A | 9/1996 | Buttner-Janz | 623/17 |
| 5,609,635 A | 3/1997 | Michelson | 623/17 |
| 5,645,596 A | 7/1997 | Kim et al. | 623/17 |
| 5,645,597 A | 7/1997 | Krapiva | 623/17 |
| 5,674,294 A | 10/1997 | Bainville et al. | 623/17 |
| 5,674,296 A | 10/1997 | Bryan et al. | 623/17 |
| 5,683,465 A | 11/1997 | Shinn et al. | 623/17 |
| 5,702,450 A | 12/1997 | Bisserie | 623/17 |
| 5,711,960 A | 1/1998 | Shikinami | 424/426 |
| 5,716,416 A | 2/1998 | Lin | 623/17 |
| 5,800,549 A | 9/1998 | Bao et al. | 623/17 |
| 5,824,093 A | 10/1998 | Ray et al. | 623/17 |
| 5,824,094 A | 10/1998 | Serhan et al. | 623/17 |
| 5,865,845 A | 2/1999 | Thalgott | 623/17 |
| 5,865,846 A | 2/1999 | Bryan et al. | 623/17 |

(List continued on next page.)

OTHER PUBLICATIONS

North American Spine Society 13 Annual Meeting, San Francisco Hilton and Towers. Oct. 28–31, 1998; Barron Lonner Md., Et. al., "Tissue Engineered Regeneration of the Intervertebral Disc".

Orthopedics Today, Jul. 2000.

"Proceedings 14th Annual Meeting" North American Spine Society, Oct. 1999.

"Proceedings 13th annual Meeting" North American Spine Society, Oct. 1998.

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Transplanted meniscus tissue is used to treat degenerative disc disease, disc herniation, or other pathologic conditions of the spine. Harvested fibrocytes are added to a meniscus removed from a suitable donor, preferably a recently deceased human. The harvested meniscus could be processed to kill the cells but preserve the extracellular matrix. Killing the cells of the allograft meniscus minimizes the risk of disease transmission and graft refection. Fibrocytes or chondrocytes would be added to the harvested meniscus extracellular matrix prior to insertion of the engineered meniscus into a patient's spine. Alternatively, the cells could be added to the harvested meniscus during or after the meniscus is placed into a patient's spine.

11 Claims, No Drawings

U.S. PATENT DOCUMENTS

| | | | |
|---|---|---|---|
| 5,888,226 A | 3/1999 | Rogozinski | 623/17 |
| 5,893,889 A | 4/1999 | Harrington | 623/17 |
| 5,899,941 A | 5/1999 | Nishijima et al. | 623/17 |
| 5,928,284 A | 7/1999 | Mehdizadeh | 623/17 |
| 6,080,579 A * | 6/2000 | Hanley et al. | 435/366 |
| 6,095,149 A * | 8/2000 | Sharkey et al. | 128/898 |
| 6,231,615 B1 | 5/2001 | Preissman | 623/23.73 |
| 6,245,107 B1 | 6/2001 | Ferree | 623/17.11 |
| 6,261,679 B1 * | 7/2001 | Chen et al. | 428/317.9 |
| 6,332,779 B1 | 12/2001 | Boyce et al. | 433/215 |
| 6,340,369 B1 | 1/2002 | Ferree | 623/17.11 |
| 6,352,558 B1 * | 3/2002 | Spector | 623/18.11 |
| 6,454,804 B1 * | 9/2002 | Ferree | 623/17.11 |

* cited by examiner

TRANSPLANTATION OF ENGINEERED MENISCUS TISSUE TO THE INTERVERTEBRAL DISC

REFERENCE TO RELATED APPLICATIONS

This application is a continuation-in-part of U.S. patent application Ser. No. 09/688,716, filed Oct. 16, 2000 U.S. Pat. No. 5,454,804, which claims priority from U.S. provisional patent application Ser. No. 60/159,488, filed Oct. 14, 1999. The entire content of each application is incorporated herein by reference.

FIELD OF THE INVENTION

This invention relates generally to the treatment of diseased or traumatized intervertebral discs, and more particularly, to the use of engineered disc tissues in conjunction with such treatment.

BACKGROUND OF THE INVENTION

Intervertebral discs provide mobility and a cushion between the vertebrae. At the center of the disc is the nucleus pulposus. The nucleus pulposus is surrounded by the annulus fibrosis, which is comprised of cells (fibrocyte-like and chondrocyte-like), collagen fibers, and non-fibrillar extracellular matrix. The components of the annulus are arranged in 15–25 lamellae around the nucleus pulposus. The fibers in the lamellae alternate their direction of orientation by 30 degrees between each band.

The annulus fibrosis has three important functions. First, the annulus contains the nucleus pulposus. Second, the annulus fibrosis, with other ligaments, connects the vertebrae of the spine. Lastly, the annulus fibrosis helps to control movement between the vertebrae.

The fibers of the annulus can tear causing pain and possible extrusion of the nucleus pulposus. Extrusion of the nucleus pulposus is known as a disc herniation. Disc herniations can compress nerves or the spinal cord resulting in arm or leg pain and dysfunction. Surgery to repair disc herniations leaves a hole in the annulus fibrosis. The hole in the annulus acts as a pathway for additional material to protrude into a nerve, resulting in a recurrence of the herniation.

To date, the treatment of tears or defects of the annulus fibrosis has relied for the most part on eliminating the defective disc or disc function. This may be accomplished by fusing the vertebra on either side of the disc. In terms of replacement, prior-art techniques replace either the nucleus or the nucleus and annulus functions. My co-pending U.S. patent application Ser. No. 09/322,516, and Patent Cooperation Treaty Application Ser. No. PCT/US/14708 describe methods and devices to occlude annular defects.

SUMMARY OF THE INVENTION

Certain of my co-pending patent applications and issued patents referenced above recognize that the annulus fibrosis augmentation and/or transplantation techniques described therein are not limited to treatment of the intervertebral disc, and that such techniques may be used to treat other tissues of the body such as the meniscus of the knee. These previous disclosures teach that a meniscus may be removed from recently deceased humans and processed to kill the cells but preserve the extracellular matrix. Fibroctyes or chondrocytes are harvested and added to the meniscus extracellular matrix, as described in my pending U.S. patent application Ser. Nos. 09/639,309, 09/628,727, 09/638,726, and 09/638,242, all of which are incorporated herein by reference.

According to this invention, the transplanted meniscus is used to treat degenerative disc disease, disc herniation, or other pathologic conditions of the spine. Since the meniscus of the knee is capable of handling the high compression and shear loads placed on the meniscus by the bones of the knee, the mechanical properties of the meniscus make it an ideal tissue to transplant to other areas of the body, including the intervertebral disc.

In this embodiment, the harvested fibrocytes are added to a meniscus removed from a suitable donor, preferably a recently deceased human. The harvested meniscus could be processed to kill the cells but preserve the extracellular matrix. Killing the cells of the allograft meniscus minimizes the risk of disease transmission and graft refection. Fibrocytes or chondrocytes would be added to the harvested meniscus extracellular matrix prior to insertion of the engineered meniscus into a patient's spine. Alternatively, the cells could be added to the harvested meniscus during or after the meniscus is placed into a patient's spine.

Cells from the meniscus could be also be harvested from a patient's knee preferably using arthroscopic surgery or other minimally invasive procedure. For example, pieces of damaged meniscus removed by an arthroscopy, could be treated to harvest the cells of the meniscus. The cultured cells from a patient's meniscus are implanted into the allograft meniscus. The engineered meniscus is surgically implanted into a patient's spine at a second surgery.

Alternatively, allograft menisci could be transplanted to a patient's intervertebral disc without adding fibrocytes. In this second embodiment, one relies on the allograft donor cells that remain alive after tissue processing and the ingrowth of the patient's tissues and cells into the allograft meniscus.

One or more allograft menisci could be placed into the intervertebral disc. The menisci could be sewn or otherwise attached to the patient's annulus fibrosis. The allograft menisci could be prepared with sutures attached to the menisci to aid the surgeon in surgery. Alternatively, allograft menisci could be morselized and injected into a patient's disc. The morselized menisci could also be added to a bag like annular augmentation device described in my co-pending U.S. patent application Ser. No. 09/690,536, incorporated herein by reference in its entirety.

DETAILED DESCRIPTION OF THE INVENTION

Broadly according to the invention, fibrocytes are harvested, cultured, added to annulus fibrosis extracellular matrix material, then sewn or otherwise placed relative to an injured or diseased disc. The annulus fibrosis cells and extracellular matrix are preferably harvested from a live human, though recently deceased human or animal donors may alternatively be used. Depending upon the extent of the harvest, the recipient may function at least in part as a donor, or the tissues from others, including fetal or embryo sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described.

Following annulus fibrosis harvest, the tissue is processed to kill the living cells. Care is taken to preserve the extracellular matrix. Guidelines for processing the harvested annulus fibrosis as described are well known to those skilled in the art. For example, the tissue could be frozen and thawed.

Fibrocytes are obtained from a tendon of the patient. For example, a palmaris longus tendon could be removed from one arm of the patient. The harvested fibrocytes are isolated and cultured using standard techniques. The harvested sterile tendon is morselized and washed with phosphate buffered saline. The cells are released from the extracellular matrix with 0.2% clostridial collagenase (Worthington CLS II, 140 u/mg) and agitated. See Klagsburn, "Methods in Enzymology, Vol. VII. The resulting suspension is filtered with 153.mu.g.nylon sieve (Tetko, Elmford, N.Y.).

The filtered solution is then centrifuged at 1800 rpm to remove the cells. The supernatant above the cells is removed with a micropipette until the cell concentration reaches $5.\times 10.^7$ cells/cc. The harvested cells are grown in Hamm's F-12 culture media, 10% fetal calf serum, L-glutamine (292.mu.g/cc), penicillin (100 u/cc), streptomycin (100.mu.g/cc), and asorbic acid (5.mu.g/cc) at 37° C. The above method is described in U.S. Pat. No. 6,060,053, which is incorporated in its entirety herein by reference.

Precursor cells of the annulus fibrosis, annulus fibrosis cells, chondrocytes, or other living cells that could function like annulus fibrosis cells or that could differentiate into cells to build a functional annulus fibrosis may also be used.

The living cells from cell culture are implanted into the donor extracellular matrix to form a living annulus fibrosis. In the preferred embodiment, the cells are injected into small holes drilled into the donor extracellular matrix.

The living cells and extracellular matrix may be added to the patient's disc immediately after combination or after a period of time to allow attachment of the cells to the matrix. Naturally, in the delayed embodiment, the cells would preferably be supported with culture media.

The engineered annulus is added to the inside or the outside of a patient's annulus. Surgical procedures to access the inner or outer surface of the annulus fibrosis are well known to those skilled in the art. The engineered annulus could be sutured, placed against, or "glued" to the patient's annulus. Platelet rich plasma combined with calcium and thrombin or "fibrin glue" could be used to glue the annular tissues together.

Additional therapeutic substances could be added to the transplanted annulus. For example, resorbable culture medium, tissue growth or differentiation factors (recombinant generated morphogenetic proteins, PDGF, TGF-β, EGF/TGF-α, IGF-I, βFGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be used.

In an alternative embodiment, living cells are not added to the harvested annulus fibrosis. The harvested annulus fibrosis is processed as described above to kill the living host annulus cells.

Although annulus fibrosis augmentation and/or transplantation is being described herein in detail, the invention is not limited to treatment of the intervertebral disc. For example, the invention could also be used to treat other tissues of the body such as the meniscus of the knee. In such cases, a meniscus would be removed from recently deceased humans. The harvested meniscus would be processed to kill the cells but preserve the extracellular matrix. Fibroctyes harvested as described above would then be added to the extracellular matrix prior to insertion of the engineered meniscus into a patient's knee. Similarly, chondrocytes could be harvested and added to the meniscus extracellular matrix as described in my pending U.S. patent Ser. Nos. 09/639,309, 09/628,727, 09/638,726, and 09/638,242.

In addition, since the meniscus of the knee is capable of handling the high compression and shear loads placed on the meniscus by the bones of the knee, the mechanical properties of the meniscus make it an ideal tissue to transplant to other areas of the body, including the intervertebral disc. The transplanted meniscus may be used in accordance with this invention to treat degenerative disc disease, disc herniation, or other pathologic conditions of the spine. Biologic tissues such as a transplanted meniscus have important advantages over disc replacement with synthetic materials. As a biologic tissue, the transplanted tissue is capable of repair. Cells that are added to the engineered meniscus, or cells that invade the meniscus after transplantation are capable of repairing and producing extracellular matrix. Artificial disc replacements made of synthetic materials are not capable of repairing themselves. Furthermore, the particles from wear of synthetic materials may promote loosening of the artificial disc. Prosthetic knees and hips often loosen as the result of particles of polyethelene that are released into the surrounding tissues.

In this embodiment, fibrocytes harvested as described herein are added to a meniscus removed from a suitable donor, preferably a recently deceased human. The harvested meniscus could be processed to kill the cells but preserve the extracellular matrix. Killing the cells of the allograft meniscus minimizes the risk of disease transmission and graft rejection. Fibrocytes or chondrocytes would be added to the harvested meniscus extracellular matrix prior to insertion of the engineered meniscus into a patient's spine. Alternatively, the cells could be added to the harvested meniscus during or after the meniscus is placed into a patient's spine.

Cells from the meniscus could also be harvested from a patient's knee preferably using arthroscopic surgery or other minimally invasive procedure. For example, pieces of damaged meniscus removed by an arthroscopy, could be treated to harvest the cells of the meniscus. The cultured cells from a patient's meniscus are implanted into the allograft meniscus. The engineered meniscus is surgically implanted into a patient's spine at a second surgery.

Alternatively, allograft menisci could be transplanted to a patient's intervertebral disc without adding fibrocytes. In this second embodiment, one relies on the allograft donor cells that remain alive after tissue processing and the ingrowth of the patient's tissues and cells into the allograft meniscus.

One or more allograft menisci could be placed into the intervertebral disc. The menisci could be sewn or otherwise attached to the patient's annulus fibrosis. The allograft menisci could be prepared with sutures attached to the menisci to aid the surgeon in surgery. Alternatively, allograft menisci could be morselized and injected into a patient's disc. The morselized menisci could also be added to a bag like annular augmentation device described in my co-pending U.S. patent application Ser. No. 09/690,536, incorporated herein by reference in its entirety.

I claim:

1. A method of treating degenerative disc disease, disc herniation, or other pathologic conditions of the spine, comprising the steps of:

harvesting meniscus tissue from a recently deceased human or other suitable donor; and placing the harvested meniscus into or onto a disc to strengthen the annulus fibrosis or to augment or replace the nucleus pulpous.

2. The method of claim 1, further comprising the steps of:

harvesting live fibrocyte or chondrocyte cells from a patient or other suitable donor; and adding the cells to the harvested meniscus during or after the meniscus is placed into a patient's spine.

3. The method of claim 1, further comprising the steps of:

relying on allograft donor cells that remain alive after tissue processing and the ingrowth of the patient's tissues and cells into the allograft meniscus.

4. The method of claim 1, wherein the meniscus is harvested from the knee of a patient or other suitable donor.

5. The method of claim 1, further including the step of placing one or more allograft menisci into the intervertebral disc.

6. The method of claim 5, wherein the menisci are sewn or otherwise attached to the patient's annulus fibrosis.

7. The method of claim 5, further including the step of morselizing the menisci and injecting the morselized menisci into a patient's disc.

8. The method of claim 7, further including the step of adding the morselized menisci to a bag-like annular augmentation device.

9. An engineered disc replacement according to the method of claim 1.

10. The engineered disc replacement of claim 9, further including one or more therapeutic substances.

11. The engineered disc replacement of claim 10, wherein the therapeutic substances include one or more of the following:

culture media, growth factors, differentiation factors, hydrogels, polymers, antibiotics, anti-inflammatory medications, or immunosuppressive medications.

* * * * *